United States Patent [19]

Drew et al.

[11] 4,260,752

[45] Apr. 7, 1981

[54] CHLORINATION PROCESS

[75] Inventors: John F. Drew, Liverpool; John A. Pepper; Victor C. Shuttlewood, both of Chester; Keith D. West, Knutsford, all of England

[73] Assignee: Chlor-Chem Limited, Cambridge, England

[21] Appl. No.: 940,505

[22] Filed: Sep. 7, 1978

[30] Foreign Application Priority Data

Sep. 8, 1977 [GB] United Kingdom ............... 37466/77

[51] Int. Cl.³ .......................................... C07D 251/28
[52] U.S. Cl. .................................................... 544/190
[58] Field of Search ........................................... 544/190

[56] References Cited

U.S. PATENT DOCUMENTS

| | | | |
|---|---|---|---|
| 3,294,797 | 12/1966 | Shallenberger et al. | 544/190 |
| 3,397,203 | 8/1968 | Symes et al. | 544/190 |
| 3,427,314 | 2/1969 | Sims et al. | 544/190 |
| 3,898,222 | 8/1975 | Hill | 544/190 |
| 3,941,784 | 3/1976 | Nelson et al. | 544/190 |
| 4,087,608 | 5/1978 | Balaban et al. | 544/190 |

*Primary Examiner*—John M. Ford
*Attorney, Agent, or Firm*—Wenderoth, Lind & Ponack

[57] ABSTRACT

The invention provides a continuous process for the production of chlorocyanuric acids by the reaction of di- and/or tri-sodiumcyanurate with chlorine in which the reaction mixture is stirred to achieve improved crystal size of the product.

6 Claims, No Drawings

CHLORINATION PROCESS

This invention relates to an improved process for the production of di- and/or tri-chlorocyanuric acids.

It has for many years been known to chlorinate cyanuric acid in the presence of caustic soda (i.e. di- or tri-sodium cyanurate) to produce chlorocyanuric acids (i.e. di- or tri-chlorocyanuric acid respectively). This process is normally carried out in two stages, i.e. a primary stage in which aqueous di- or tri-sodium cyanurate is reacted with the chlorine-containing vent gases from the secondary stage, and a secondary stage in which the partially chlorinated product from the primary stage is reacted with further chlorine. These reactions are difficult to operate satisfactorily on a plant scale and are associated with considerable problems, notably blockage of the outlet ports by large agglomerates of product, production of a product which is difficult subsequently to filter or centrifuge off, poor efficiency of conversion of di- or tri-sodium cyanurate to the corresponding chlorocyanuric acid, crystallisation of the product in unwanted areas, e.g. in circulation lines, and inconsistent product crystal size.

We have now found that a number of these problems can be partly or wholly overcome.

Accordingly, in one aspect, this invention provides a continuous process for the production of di- and/or tri-chlorocyanuric acid, which comprises reacting chlorine with di- and/or tri-sodium cyanurate in an aqueous medium, characterised in that the reaction mixture is subjected to agitation by means of a stirrer.

We have found that the above problems may be mitigated by effecting an appropriate speed of stirring having regard to the prevailing conditions. The speed of the stirrer is thus preferably adjustable. In particular, we have found that the efficiency of conversion of di- and/or tri-sodium cyanurate to di- and/or tri-chlorocyanuric acid may surprisingly be increased relative to known large scale production processes by effecting an appropriate speed of stirring, and that the crystal size of the product may also be increased relative to known processes and made more consistent by the same means. Indeed, we have found that the process may be made sufficiently efficient to render otiose the primary chlorination stage of the prior-art processes. Accordingly, it is a preferred feature of the invention that it be performed in a single chlorination stage, since this naturally avoids the need for some of the expensive capital equipment required by the prior-art processes.

The speed of stirring required depends upon a very large number of variables, for example reactor and stirrer size, the purity of the feed solution of di- and/or tri-sodium cyanurate, the rate of flow of that feed solution, the temperature thereof, and the pH in the reaction mixture. It is impossible to state a quantitative relationship between these factors and the speed of stirring required, but in general this is not of importance. In usual practice on any one plant, the reactor and stirrer sizes, the purity and temperature of the feed solution and the pH and temperature of the reaction mixture are kept very much constant, the only variable of any significance being the rate of flow of the feed solution.

The rate of flow of the feed solution frequently is varied dependent upon demand for the product or availability of subsequent plant for processing it or other bottlenecks which occur from time to time on the plant. Hitherto, when variations have been made in the rate of flow of the feed solution, variations have been observed in the product. Such variations in the product can be reduced or eliminated in accordance with a preferred aspect of the invention by varying the stirrer speed in relation to the rate of flow of the feed solution, increasing it when the flow rate increases and decreasing it when the flow rate decreases. Again, a simple relationship between rate of flow of feed solution and optimum speed of stirring required has not been observed, but acceptable results may as a first approximation be obtained by determining an optimum stirrer speed for a particular flow rate and varying it in direct proportion to the flow rate as the flow rate varies.

For any one plant, the necessary adjustment of stirrer speed is best determined empirically by conducting tests at various flow rates. Such tests are well within the competence of those skilled in the art, and eliminate other variables peculiar to that plant which might affect the crystal size of the product. In general, an appropriate stirrer speed is one that produces a product which is easily filterable. Such products normally have a mean crystal size not below 50 microns in length and not below 10 microns in width.

With too low a stirrer speed the crystal size falls below this value and the efficiency of conversion of di- and/or tri-sodium cyanurate to di- and/or tri-chlorocyanuric acid is reduced. When too high a stirrer speed is employed the crystal size of the product also falls below the above value.

As stated above, we prefer to employ a single stage chlorination. However, when a two-stage chlorination process is used, at least the second stage should be agitated in accordance with the invention. More preferably, both stages are agitated in accordance with the invention since otherwise there exists a tendency for a mixture of sodium chlorocyanurates to be precipitated in the first stage.

The chlorine inlet is preferably located close to the blades of the stirrer in the reactor, since this further improves the process efficiency.

The or each stirred reactor employed is preferably of at least 100 gallons capacity.

Preferably, the reaction is carried out at a temperature of from 15° to 40° C., especially 26° to 32° C., and at a pH of from 2 to 3.8, especially 2.5 to 3.5.

The stirrer may be provided with an infinitely variable gear box, and may, for example, be a stabilised top hung flat bladed turbine. The seal between the stirrer shaft and the reaction vessel may if desired or necessary be such as to substantially prevent the escape of chlorine, and may be, for example, a water flushed double seal. The stirrer itself and the reaction vessel should be made of a chlorine resistant material, e.g. glass, surface coated steel, a plastics material, titanium or another material which is chlorine resistant under the reaction conditions employed. The reaction vessel itself is preferably provided with internal baffles to assist in the agitation.

The stirrer assembly is preferably such that there is as little whip as possible on the shaft, thus enabling a tight seal to be achieved if desired. Thus the use of a heavy and balanced stirrer and a large diameter shaft is preferred.

We have found that by using the process described above it is possible to produce consistently large crystals of di- and/or tri-chlorocyanuric acid which are easily separated from the reaction mixture. Thus the process of the invention can produce crystalline monoclinic dichlorocyanuric acid of mean crystal size from about 60 to 300 microns in length and from about 10 to 25 microns in diameter, and trichlorocyanuric acid typically as clusters of approximately 400 microns diameter. This invention provides per se di- and/or trichlorocyanuric acid the mean crystal size of which is greater than 60×10, and more preferably greater than 100×10, microns. The large crystal or cluster size enables easier filtration of the product with less water than conventionally in the filter cake. In turn, this enables greater efficiency of crystal separation by centrifugation and in subsequent drying. Typical prior art processes have produced crystals of approximately 50×10 microns.

The invention is illustrated but in no way limited by the following Examples.

EXAMPLE 1

The apparatus used comprises a 700 gallon titanium reactor provided with internal baffles, a variable speed stirrer, a chlorine feed (the chlorine feed being inserted below the stirrer in order to provide good gas dispersion), an aqueous disodium cyanurate feed, a system for the continuous removal of reaction product, a cooling jacket, an external heat exchanger and a vent pipe for vent gases. The pH of the reaction mixture in the reactor was maintained between 2.5 and 3.5. Using the above apparatus and reaction conditions the results shown in the following table were obtained:

| A | B | C | D | E |
|---|---|---|---|---|
| 3.0 | 290 | 200 × 20 | 89.6 | 83.3 |

A relative feed rate of disodium cyanurate feed solution (a relative feed rate of 3.0 giving a residence time in the reactor of about 40 minutes).
B Stirrer speed in RPM.
C Mean crystal size in microns of the dichlorocyanuric acid product.
D Average yield after filtration and drying as % theory on input cyanuric acid.
E Average yield after filtration and drying as % theory on input chlorine.

EXAMPLE 2

A run similar to that of Example 1 was also carried out in in which run the feed material was aqueous trisodium cyanurate and the product was trichlorocyanuric acid. The corresponding results obtained were as follows:

| A | B | C | D |
|---|---|---|---|
| 4.0 | 290 | 400 × 400 (clusters) | 84.0 |

EXAMPLE 3

A run similar to that of Example 1 was also carried out, in which the vent pipe from the reactor of Example 1 led into a 500 gallon primary reactor, the partially chlorinated product from which was fed to the reactor of Example 1. The primary reactor was fed with aqueous disodium cyanurate solution.

The corresponding results obtained were as follows:

| A | B | C | D | E |
|---|---|---|---|---|
| 1.0 | 133 | 70 × 10 | | |
| 1.0 | 120 | 150 × 10 | | |
| 1.0 | 96 | 100 × 10 | 86.5 | 82.1 |
| 1.0 | 90 | 75 × 10 | | |
| 1.0 | 92 | 180 × 15 | | |
| 1.5 | 92 | 200 × 20 | — | |
| 2.0 | 145 | 50 × 10 | | |
| 2.0 | 108 | 170 × 12 | | |
| 2.0 | 136 | 200 × 20 | | |
| 2.0 | 140 | 100 × 15 | 86.5 | 82.1 |
| 2.1 | 140 | 150 × 20 | | |
| 2.2 | 120 | 130 × 20 | | |
| 2.2 | 150 | 170 × 15 | | |

EXAMPLE 4

For comparison the following typical results were obtained using the same apparatus and reaction conditions as in Example 3 but employing a circulatory pump instead of the stirrer.

| A | B | C | D | E |
|---|---|---|---|---|
| 2.0 | — | 50 × 10 | 75.0 | 71.0 |

These results represent about the best that could be achieved by prior-art processes.

We claim:
1. A continuous process for the production of at least one member selected from the group consisting of dichlorocyanuric acid and trichlorocyanuric acid, which comprises reacting chlorine with at least one member selected from the group consisting of disodium cyanurate and trisodium cyanurate in an aqueous medium, characterised in that the reaction mixture is subjected to agitation by means of a stirrer, the spped of which is varied during the process, and all reaction parameters are maintained substantially constant except that the flow rate of the cyanurate feed solution to the reaction is varied, and the speed of the stirrer is increased as the flow rate increases and is decreased as the flow rate decreases, so as to give a product having a mean crystal size greater than 60×10 microns.

2. A process according to claim 1, wherein the speed of the stirrer is such as to give a product having a mean crystal size greater than 100×10 microns.

3. A process according to claim 1, wherein the or each reactor in which the stirring is effected is of at least 100 gallons capacity.

4. A process according to claim 1, wherein the chlorination is effected in a single stage only.

5. A process according to claim 1, wherein the chlorination is effected at a temperature of from 15° to 40° C.

6. A process according to claim 1, 2, 3, 4 or 5, wherein the chlorination is effected at a pH from 2 to 3.8.

* * * * *